US010011774B2

(12) United States Patent
Bianchina et al.

(10) Patent No.: US 10,011,774 B2
(45) Date of Patent: Jul. 3, 2018

(54) REACTOR VESSEL, SYSTEM AND METHOD FOR REMOVING AND RECOVERING VOLATILIZING CONTAMINANTS FROM CONTAMINATED MATERIALS

(71) Applicant: OSS MANAGEMENT SERVICES (PTY) LIMITED, Germiston, Gauteng (ZA)

(72) Inventors: Leonard Benjamin Bianchina, Germinston (ZA); Ian Nigel Tunnicliffe, Shropshire (GB)

(73) Assignee: OSS MANAGEMENT SERVICES (PTY) LIMITED, Germiston (ZA)

( * ) Notice: Subject to any disclaimer, the term of this patent is extended or adjusted under 35 U.S.C. 154(b) by 551 days.

(21) Appl. No.: 14/417,320

(22) PCT Filed: Jul. 25, 2013

(86) PCT No.: PCT/IB2013/001619
§ 371 (c)(1),
(2) Date: Jan. 26, 2015

(87) PCT Pub. No.: WO2014/016666
PCT Pub. Date: Jan. 30, 2014

(65) Prior Publication Data
US 2015/0240164 A1 Aug. 27, 2015

(30) Foreign Application Priority Data
Jul. 26, 2012 (ZA) ................................ 2012/05660

(51) Int. Cl.
*A61L 9/00* (2006.01)
*C10B 19/00* (2006.01)
(Continued)

(52) U.S. Cl.
CPC ................ *C10B 19/00* (2013.01); *C10B 1/04* (2013.01); *H05B 6/129* (2013.01)

(58) Field of Classification Search
CPC ... A61L 2/00; A61L 11/00; B09B 3/00; A62D 3/00; C02F 1/00
(Continued)

(56) References Cited

FOREIGN PATENT DOCUMENTS

| | | |
|---|---|---|
| JP | 2003-320337 | 11/2003 |
| JP | 2005-083634 | 3/2005 |

(Continued)

OTHER PUBLICATIONS

Japanese Patent Office English Translation for JP 2005083634 A (Description, Claims, and Drawings).*

(Continued)

*Primary Examiner* — Monzer R Chorbaji
(74) *Attorney, Agent, or Firm* — Nixon & Vanderhye P.C.

(57) ABSTRACT

The invention relates to a reactor, a system and a method for treating and recovery of liquid and/or solid waste materials and by-products from industrial manufacturing and production operations, such as volatilizing organic compounds, by converting these materials into valuable materials which could be recycled and re-used, while at the same time minimizing any residue for final disposal to landfill or incineration. The invention includes an insulated, magnetic, electrically conductive reactor vessel [10] for receiving and treating a contaminated load, the reactor being characterized therein that it is operated under pyrolysis conditions and is heated by radio frequency induction of eddy currents into the reactor vessel [10].

24 Claims, 2 Drawing Sheets

(51) Int. Cl.
*H05B 6/12* (2006.01)
*C10B 1/04* (2006.01)

(58) Field of Classification Search
USPC ...................................... 422/32, 186.01, 307
See application file for complete search history.

(56) References Cited

FOREIGN PATENT DOCUMENTS

| | | | | |
|---|---|---|---|---|
| JP | 2005083634 A | * | 3/2005 | .............. F27B 14/06 |
| JP | 2005-127682 | | 5/2005 | |

OTHER PUBLICATIONS

International Search Report for PCT/IB2013/001619, dated Dec. 2, 2013, two pages.

* cited by examiner

REACTOR VESSEL, SYSTEM AND METHOD FOR REMOVING AND RECOVERING VOLATILIZING CONTAMINANTS FROM CONTAMINATED MATERIALS

This application is the U.S. national phase of International Application No. PCT/IB2013/001619 filed 25 Jul. 2013 which designated the U.S. and claims priority to South African Patent Application No. 2012/05660 filed 26 Jul. 2012, the entire contents of each of which are hereby incorporated by reference.

INTRODUCTION

This invention relates to a reactor, a system and a method for on-site and/or off-site treating and recovery of liquid and/or solid waste materials and by-products from industrial manufacturing and production operations, such as volatilizing organic compounds, by converting these materials into valuable materials which could be recycled and re-used, while at the same time minimizing any residue for final disposal to landfill or incineration. Without derogating from the generality of the foregoing, the invention provides for the treatment and recovery of hydrocarbon-containing and contaminated solids, liquids (Newtonian and Non-Newtonian), oil in water emulsions, water in oil emulsions, chlorinated and non-chlorinated solvents, polymeric hydrocarbons, products made from or derived from cellulose, biomass or the like (thus producing the by-product), synthetic gas, pyrolysis oil, water and carbon char. After treatment of these materials, the synthetic gas and pyrolysis oil may be re-useable components as produced, the water may be re-used after further treatment, and any remaining carbon char is substantially free of hydrocarbons and aqueously extractable contaminants.

BACKGROUND TO THE INVENTION

In industrialized societies the occurrence of hazardous materials spills has become common place and various technologies have been developed to deal with these types of situations. Such spills sometimes occur at sea, but more often occur on land or even underneath the ground surface. For example, underground gasoline tanks may leak or solvents used in industrial processes may be discharged illegally into waste water or sumps or directly onto the ground. In any case, the hazardous material, typically a volatilizing organic compound, may propagate great distances through the ground and even enter ground water aquifers. It will be appreciated that the resulting environmental impact may be devastating.

Many hazardous materials found at these sites are stable, do not undergo environmental degradation at reasonably fast rates, have high boiling points and are considered toxic at very low concentration levels. Accordingly, such materials can bio-accumulate in various species of the food chain at concentrations higher than what is found in the environment.

Several techniques have been proposed to deal with the treatment and recovery of such volatilizing organic compounds and other contaminants. These include everything from various vacuum techniques, where soil is removed and treated, to on-site treatment of contaminated soil. Another technique is pyrolysis, which has been used for the thermal destruction of many contaminated materials. Known techniques, however, suffer from a range of shortcomings.

One such shortcoming is the high costs associated with removing and cleaning contaminated soil by means of commercially available techniques and systems, because of the inherent characteristics and operating parameters of these techniques and systems.

Another shortcoming is that known treatment techniques often do not provide an effective solution to the problem, as it is inadequate to remove the hazardous materials completely, leaving behind small amounts of the hazardous materials even in the treated and "cleaned" soil, which continues to be a potential source of an environmental disaster.

Also, with known soil cleaning techniques often only a limited volume of ground soil can be treated at a time. This limitation not only increases costs as a result of repeated cleaning cycles, as well as with respect to the need for safe storage and transport of contaminated soil, but also increases the time that it takes to clean a contaminated area sufficiently.

A further disadvantage of many treatment options is that the contaminated materials are heated to temperatures which vaporise and/or thermally destroy the contaminants. These processes do not allow for the recovery and/or potential re-use of the contaminants.

A need exists for a method and apparatus for efficiently and rapidly removing hazardous materials, including volatilizing organic compounds, from contaminated material without excessive contaminant discharge to the atmosphere, and for doing so at a reasonable cost, while at the same time recovering re-usable materials.

SUMMARY OF THE INVENTION

The invention uses radio frequency induction heating in a pyrolysis system for removing and recovering volatizing contaminants from a contaminated material load.

According to a first aspect of the invention there is provided an insulated, magnetic, electrically conductive reactor vessel for use in removing and recovering volatilizing contaminants from contaminated materials, including, but not limited to, spent grease and catalysts, waste solvents and various sludges, while simultaneously minimising residue for final disposal to landfill or incineration, the reactor vessel being characterised therein that it is operated under pyrolysis conditions and is heated by radio frequency induction of eddy currents into the reactor vessel, the reactor vessel comprising—

- a reactor base;
- a cylindrical reactor wall extending upright from the base;
- a removable lid dimensioned to rest on the cylindrical wall for sealing the reactor vessel; the reactor base, cylindrical reactor wall and removable lid together defining a reactor volume for holding a contaminated material load;
- a transmitter in the form of a first heating element arranged approximate a circumference of the reactor vessel and magnetically coupled to the reactor vessel; and
- at least one exhaust for permitting egress of gasses and steam from the reactor vessel.

The reactor base, cylindrical reactor wall and removable lid may be covered by heat-insulating material.

The reactor vessel may be a ferromagnetic or ferrimagnetic electrically conductive reactor vessel.

The first heating element may be an external induction coil which is magnetically coupled to the cylindrical reactor wall and which acts as the transmitter, in the process rendering the reactor vessel a receiver. In particular, the external induction coil may be connected to an external surface of the cylindrical reactor wall, such that the heat-insulating material is trapped between the cylindrical reactor wall and the external induction coil. The external induction coil may extend substantially the height of the reactor vessel so as to cover at least most, preferably all, of the cylindrical reactor wall between the reactor base and the removable lid.

The external induction coil may be connected to a power supply for inducing eddy currents into the reactor vessel from the external induction coil around the reactor vessel so as to heat a contaminated material load inside the reactor volume by means of radio frequency induction.

In one embodiment of the invention the reactor vessel further may include a second heating element which is removably insertable into the reactor vessel and magnetically coupled to the first heating element. The second heating element may be an internal induction coil arranged co-axially with the reactor vessel and the external induction coil. The internal induction coil may be located within a blind tube in the center of the reactor vessel. The blind tube may be an elongate metallic tube extending upright through the reactor base and into the reactor volume, positioned coaxially with the reactor vessel and dimensioned to house the internal induction coil therein, the blind tube being closed at its one end which protrudes into the reactor volume, so as to insulate the internal induction coil from a contaminated material load, and being open at its opposite end for receiving the internal induction coil therein.

The internal induction coil may be connected in series with the external induction coil around the circumference of the reactor vessel, thereby magnetically coupling the external and internal induction coils with the blind tube in the center of the reactor vessel, which creates induced currents into the blind tube. In this way heat is transferred radially outwards from the blind tube in the center of the reactor vessel, as well as radially inwards from the cylindrical reactor wall.

In yet a further alternative embodiment of the invention, the reactor vessel also may include one or more conducting plates connected to and extending radially outwardly from the blind tube and the internal induction coil for increasing thermal conduction through a contaminated material load. The reactor vessel may include four equally spaced conducting plates connected to and extending radially outwardly from the blind tube and terminating in hollow upright tubes located approximate and parallel to the cylindrical reactor wall.

According to a second aspect of the invention there is provided a sealed, batch-driven system for removing and recovering volatilizing contaminants from contaminated materials, including, but not limited to, spent grease and catalysts, waste solvents and various sludges, while simultaneously minimising any residue for final disposal to landfill or incineration, the system being characterised therein that it is operated as a pyrolysis system and is heated by radio frequency induction, the system comprising—

- an insulated, magnetic, electrically conductive reactor vessel as described hereinbefore;
- a vapour extraction system for removing vapours from within the reactor vessel;
- a condenser arranged in flow communication with the reactor vessel for condensing removed vapours; and
- a power supply for supplying low frequency power to create eddy currents within the reactor vessel so as to heat a contaminated material load inside the reactor volume by means of radio frequency induction; the arrangement being such that a radio-frequency alternating current is passed between the first heating element and the reactor vessel, in the absence of oxygen, for volatilising the contaminants within the material.

The system may be adapted for removing and recovering volatilizing contaminants from contaminated materials for purposes of re-use.

The power supply may include an AC to DC converter for converting three-phase AC mains supply voltage from a supply frequency of 50 Hz to DC power. The converter may supply a variable DC voltage, a fixed DC voltage or a variable DC current.

The power supply further may include an inverter for converting the DC power to single phase AC output. In particular, the DC current may be fed to the inverter which converts the DC supply to a single phase AC output at a frequency of between 4 KHz and 100 KHz.

The inverter may include a semi-conductor relay which is configured as an H-bridge. The H-bridge may include four legs, each associated with a switch. The output circuit may be connected across the center of the H-bridge. When the relevant two switches are closed, current may flow through the load in one direction. When the same switches are opened and the opposing two switches closed, current may be allowed to flow in the opposite direction. By precisely timing the opening and closing of the switches, it is possible to sustain oscillations in the load circuit. This is fed to the external induction coil whereupon mutual inductance between the external induction coil and the reactor vessel (and the internal induction coil inside the vessel, if it is present) creates a magnetic coupling. This induction causes eddy currents to be induced into the reactor vessel from the external induction coil around the reactor vessel and the internal induction coil in the blind tube in the center of the reactor vessel.

The system also may include a vacuum, not only so as to increase relative volatility of key hydrocarbon components in a contaminated load, thus creating a higher yield in recovered hydrocarbons, but also to reduce the temperature requirements under which the system would otherwise function. Operating the system under vacuum conditions reduces running costs, increases distillation of hydrocarbon fractions, and reduces cycle times.

According to further aspect of the invention there is provided a pyrolysis method for removing and recovering volatilizing contaminants from contaminated materials, including, but not limited to, spent grease and catalysts, waste solvents and various sludges, while simultaneously minimising any residue for final disposal to landfill or incineration, the method being characterised therein that heat is supplied by radio frequency induction of eddy currents, the method comprising the steps of—

- providing a sealed, batch-driven pyrolysis system as described hereinbefore;
- loading the reactor vessel with a contaminated material load;
- sealing the reactor vessel with the removable lid;
- inducing eddy currents into the reactor vessel, in the absence of oxygen, from the external induction coil for volatilising contaminants within the contaminated material load by means of radio frequency induction heating; and
- collecting vapour and recoverable products in the condenser as condensates.

The method further may include the step of operating the sealed, batch-driven pyrolysis system under vacuum conditions.

It will be appreciated that different waste materials or by-products require different temperatures during the treatment process. Temperatures may vary from 175° C. up to about 850° C. Upon heating, contaminants in the material load are volatilized and residual oxygen is displaced from the reactor vessel, allowing heat treatment of the contaminated material load to take place in the absence of oxygen.

The moisture content of a contaminated material load may vary between 20% and 90%. After treatment according to the claimed invention, remaining residue is either in a dry format, or may remain in a viscous liquid format of about 5% to 10% moisture content by volume.

Recovered products may be returned to a supply chain for re-use, for example recovered oil may be refined and re-used as a burning fuel or other energy source; metals, precious metals and minerals may be extracted from the remaining residue; and oil may be recycled from spent and off-spec grease.

Radio frequency ("RF") has a rate of oscillation in the range of about 30 KHz to 300 GHz, which corresponds to the frequency of electrical signals normally used to produce and detect radio waves. Radio-frequency induction is the use of a radio frequency magnetic field the transfer of energy by means of electromagnetic induction in a near field.

This invention exploits a so-called near field of electromagnetic radiation. A near field, far field and transition zone are regions in the field of electromagnetic radiation that emanates from a radiating antenna or transmitter, which in this invention is the external induction coil around the reactor vessel. Certain behavioral characteristics of electromagnetic fields dominate at one distance from the transmitter, while a completely different behavior can dominate at another location. Defined boundary regions categorize these behavioral characteristics. The regional boundaries are always measured as a function of a ratio of the distance from the radiating source (i.e. external induction coil) to the wavelength of the radiation.

This invention provides intentionally magnetically coupling the transmitter with the reactor vessel, as well as with the internal induction coil placed inside the vessel, in those embodiments where the internal induction coil is present. Two conductors are referred to as "mutual-inductively coupled" or "magnetically coupled" when they are configured such that a change in current flow through one wire (the external induction coil) induces a voltage across the ends of the other wire (i.e. either the reactor vessel alone, or both the reactor vessel and internal induction coil, in embodiments where the latter is present) through electromagnetic induction. The amount of inductive coupling between two conductors is measured by their mutual inductance.

The coupling between two wires can be increased by winding them into coils and placing them close together on a common axis, so the magnetic field of one coil (external induction coil) passes through the other coil (reactor vessel). The two coils may be physically contained in a single unit, as in the primary (external induction coil) and secondary sides (reactor vessel) of a transformer, or may be separated.

Eddy currents (also called Foucault currents) are currents induced in conductors, opposing the change in flux that generated them. It is caused when a conductor is exposed to a changing magnetic field due to relative motion of the field source and conductor, or due to variations of the field with time. This can cause a circulating flow of electrons, or a current, within the body of the conductor. These circulating eddies of current create induced magnetic fields that oppose the change of the original magnetic field due to Lenz's law, causing repulsive or drag forces between the conductor and the magnet. The stronger the applied magnetic field, or the greater the electrical conductivity of the conductor, or the faster the field that the conductor is exposed to changes, then the greater the currents that are developed and the greater the opposing field. Eddy currents, like all electric currents, generate heat as well as electromagnetic forces. In the present invention this heat is harnessed for heating the reactor vessel.

Whilst the magnetic coupling is greatest between the external induction coil and the reactor vessel, eddies are also induced into any ferromagnetic material that may be inside the vessel, such as the internal conduction coil, blind tube and conduction plates, which aids thermal conduction through the liquid or solid contaminated material load that is being treated.

This process and apparatus may also be used to process oil filters. In such applications, the oil filters act as the receiver and will themselves become magnetically coupled with the external induction coil around the reactor vessel, as well as with the internal induction coil located within the central blind tube (in applications where the internal induction coil is present). The same could be said for tyres, where the tyre steel banding would produce the same effect.

SPECIFIC EMBODIMENT OF THE INVENTION

The reactor vessel of the invention will now further be described by way of non-limiting example only and with reference to the accompanying drawings in which—

Figure 1:
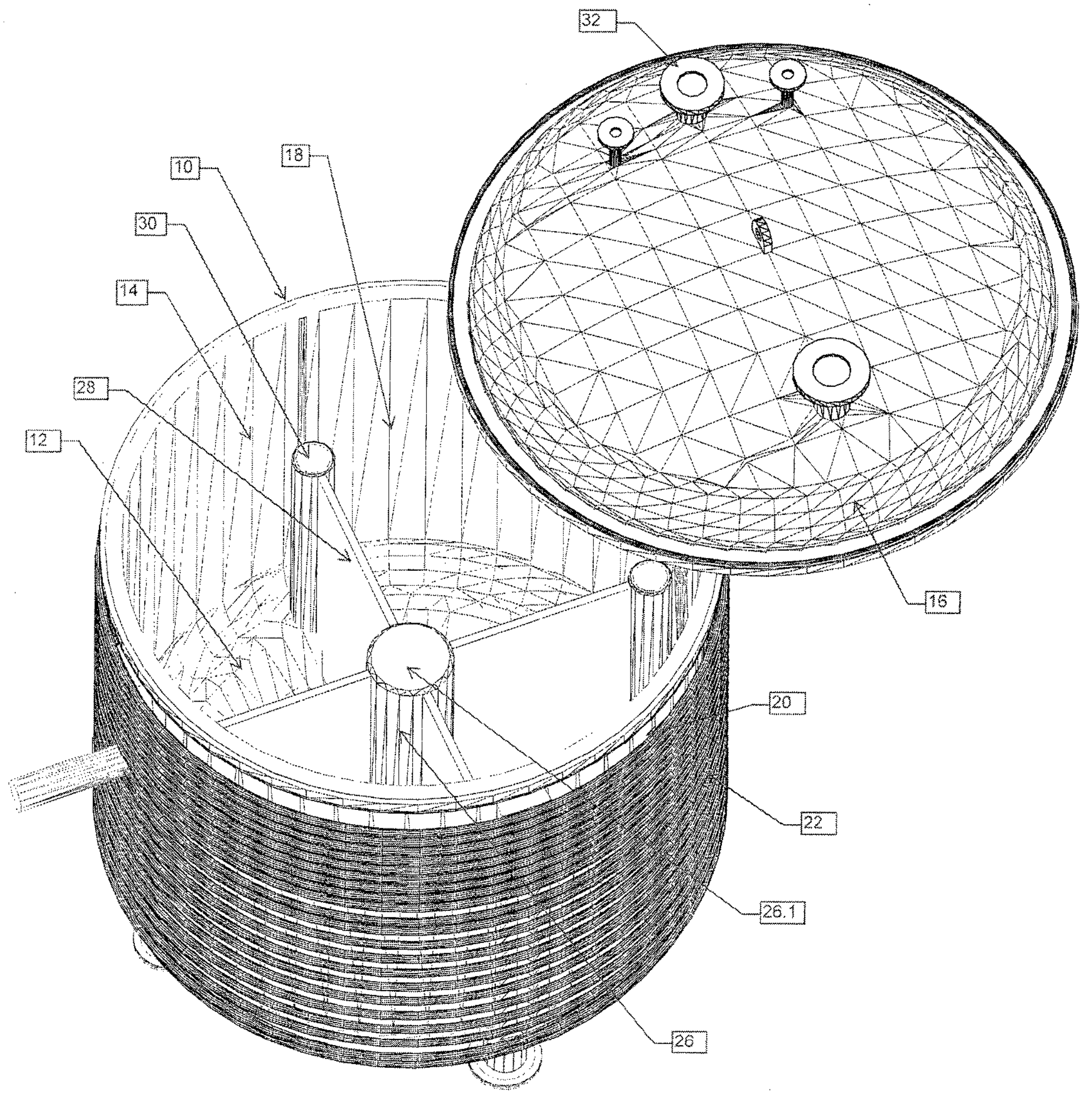
FIG. 1 is a perspective view of a reactor vessel according to one embodiment of the invention, the reactor vessel being illustrated with its removable lid in a partially open position, and including a blind tube and four conducting plates.
Figure 2:
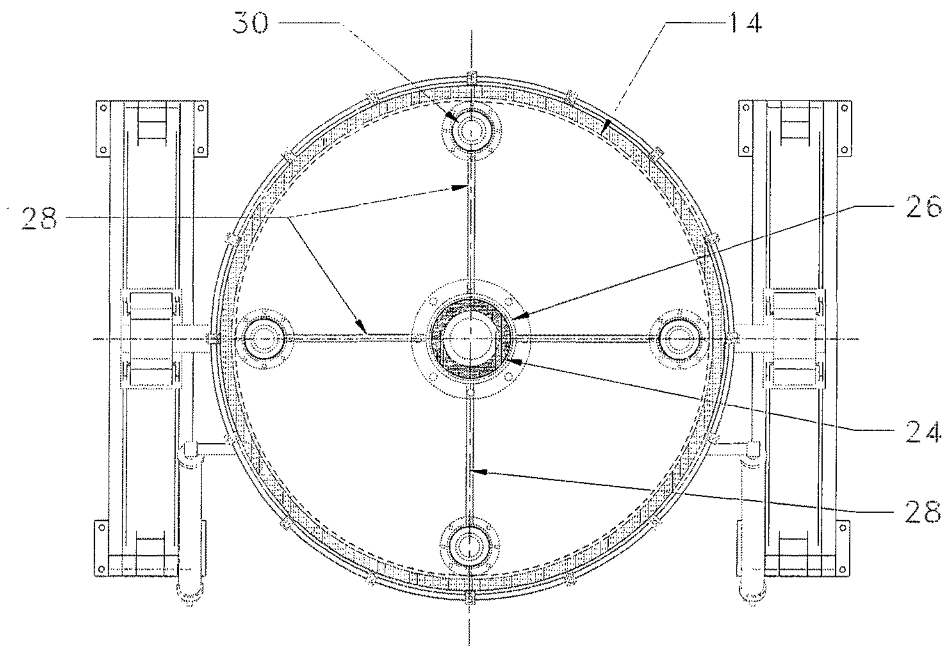
FIG. 2 is a plan view from above of the reactor vessel of FIG. 1, with the lid removed.
Figure 3:
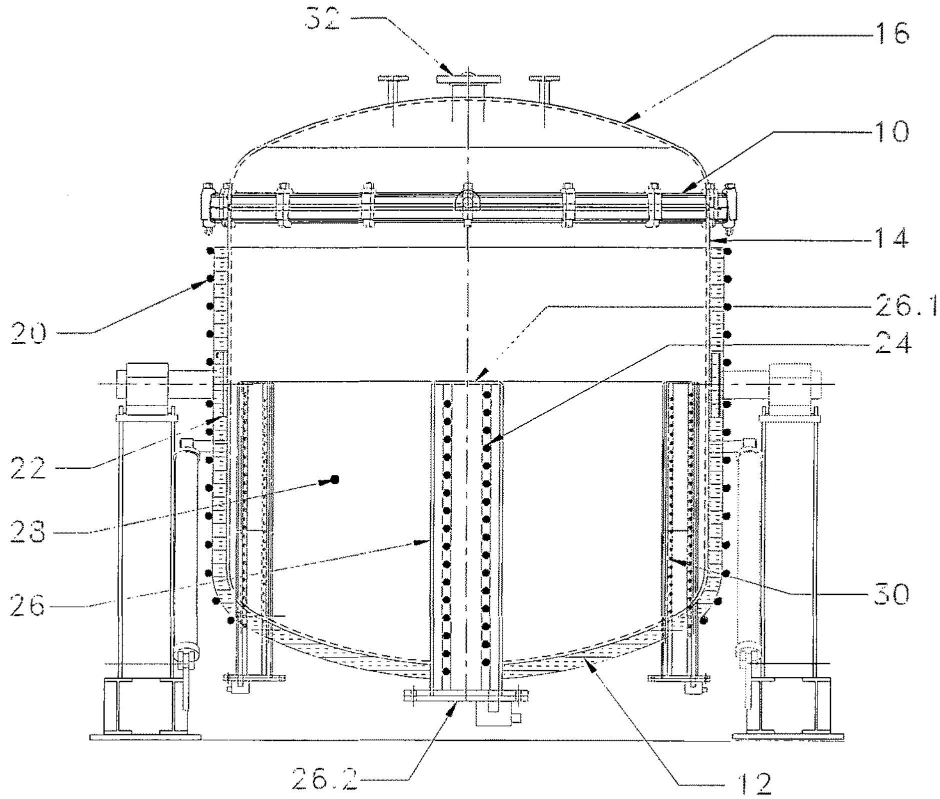
FIG. 3 is a cross-sectional side view of the reactor vessel of FIG. 1, with the lid in a closed position.

An insulated, magnetic, electrically conductive reactor vessel according to the invention is designated by reference numeral [10]. The reactor vessel [10] comprises a reactor base [12]; a cylindrical reactor wall [14] extending upright from the base [12]; and a removable lid [16] dimensioned to rest on the cylindrical reactor wall [14] for sealing the reactor vessel [10]. The reactor base [12], cylindrical reactor wall [14] and removable lid [16] together define a reactor volume [18] for holding a contaminated material load (not shown) in use. The reactor base [12], cylindrical reactor wall [14] and removable lid [16] are covered by heat-insulating material [20].

The reactor vessel [10] further comprises a transmitter in the form of a first heating element [22] arranged approximate a circumference of the reactor vessel [10] and magnetically coupled to the reactor vessel [10]. In particular, the first heating element is an external induction coil [22] which is magnetically coupled to the cylindrical reactor wall [14] and which acts as the transmitter, in the process rendering the reactor vessel [10] a receiver. More particularly, the external induction coil [22] is connected to an external surface of the cylindrical reactor wall [14] such that the heat-insulating material [20] is trapped between the cylindrical reactor wall [14] and the external induction coil [22]. The external induction coil [22] extends substantially the height of the reactor vessel [10] so as to cover at least most, preferably all, of the cylindrical reactor wall [14] between the reactor base [12] and the removable lid [16].

The external induction coil [22] is connected to a power supply (not shown) for inducing eddy currents into the reactor vessel [10] from the external induction coil [22] around the reactor vessel [10] so as to heat a contaminated material load (not shown) inside the reactor volume [18] by means of radio frequency induction.

In the illustrated embodiment of the invention the reactor vessel [10] further includes a second heating element [24] which is removably insertable into the reactor vessel [10] and magnetically coupled to the first heating element [22]. The second heating element [24] is an internal induction coil [24] arranged co-axially with the reactor vessel [10] and the external induction coil [22].

The internal induction coil [24] is located within a blind tube [26] in the center of the reactor vessel [10]. The blind tube [26] is an elongate metallic tube extending upright through the reactor base [12] and into the reactor volume [18], positioned coaxially with the reactor vessel [10] and dimensioned to house the internal induction coil [24] therein. The blind tube [26] is closed at its one end [26.1] which protrudes into the reactor volume [18], so as to insulate the internal induction coil [24] from a contaminated material load (not shown) in use, and is open at its opposite end [26.2] for receiving the internal induction coil [24] therein.

The internal induction coil [24] is connected in series with the external induction coil [22] around the circumference of the reactor vessel [10], thereby magnetically coupling the external and internal induction coils [22, 24] with the blind tube [26] in the center of the reactor vessel [10], which creates induced currents into the blind tube [26]. In this way heat is transferred radially outwards from the blind tube [26] in the center of the reactor vessel [10], as well as radially inwards from the cylindrical reactor wall [14], into the contaminated material load (not shown).

In the illustrated embodiment of the invention, the reactor vessel [10] further includes four, equally spaced conducting plates [28] connected to and extending radially outwardly from the blind tube [26] and the internal induction coil [24] for increasing thermal conduction through a contaminated material load. The four conducting plates [28] are connected to and extend radially outwardly from the blind tube [26], terminating in hollow upright tubes [30] located approximate and parallel to the cylindrical reactor wall [14].

It will be appreciated that the internal conduction coil [24] and conducting plates [28] are optional additions to the reactor vessel [10].

The reactor vessel [10] also includes at least one exhaust [32], which is located in the removable lid [16], for permitting egress of gasses and steam from the reactor vessel [10] to the condenser (not shown).

The invention has proven to be effective in treating, inter alia, lower alcohols, lower alkanes, lower alkenes, alkynes and aromatics or mixtures or combinations thereof, which are treated under conditions of pressure, vacuum and temperature to reduce the components to syngas, water, pyrolysis oil and carbon char. In particular, the invention provides a method for removing contaminants, including lower alkanes, lower alkenes, alkynes or mixtures or combinations thereof from substrates unaffected by temperatures up to 800° C., with sufficient time to achieve a desired degree of separation of the mixture into a solid residue, a water insoluble liquid, a gaseous phase and an aqueous phase, derived from thermo-chemical destruction in an atmosphere substantially free from oxygen and heated by radio-frequency induction of eddy currents into the reactor vessel material of construction.

The present invention furthermore provides, inter alia, a solid and aqueous residue substantially free of organic and/or non-organic water soluble components and hydrocarbons; and a water-insoluble liquid and hydrocarbon residue substantially free of solids and organic and/or non-organic water soluble components; derived from thermo-chemical destruction in an atmosphere substantially free from oxygen and heated by radio-frequency induction of eddy currents into the reactor vessel material of construction.

The present invention has also been proven effective in the destruction of drilling fluids, oil contaminated soil, oil pit material, used grease, used lube oils, hydraulic oils, tar sands, refinery bottoms and tanker bottoms, derived from thermo-chemical destruction in an atmosphere substantially free from oxygen and heated by radio-frequency induction of eddy currents into the reactor vessel material of construction.

It will be appreciated that other embodiments of the invention may be possible without departing from the spirit or scope of the invention as defined in the claims.

The invention claimed is:

1. An insulated, magnetic, electrically conductive reactor vessel for use in removing and recovering volatilizing contaminants from contaminated materials, while simultaneously minimising residue for final disposal to landfill or incineration, the reactor vessel being characterised therein that it is operated under pyrolysis conditions and is heated by radio frequency induction of eddy currents into the reactor vessel, the reactor vessel comprising—a reactor base;

a cylindrical reactor wall extending upright from the base;

a removable lid dimensioned to rest on the cylindrical reactor wall for sealing the reactor vessel; the reactor base, cylindrical reactor wall and removable lid together defining a reactor volume for holding a contaminated material load;

a transmitter in the form of a first heating element arranged approximate a circumference of the reactor vessel and magnetically coupled to the reactor vessel;

a second heating element which is removably insertable into the reactor vessel and magnetically coupled to the first heating element; and at least one exhaust for permitting egress of gasses and steam from the reactor vessel.

2. The reactor vessel according to claim 1 in which the reactor base, cylindrical reactor wall and removable lid is covered by heat-insulating material.

3. The reactor vessel according to claim 2 in which the external induction coil is connected to an external surface of the cylindrical reactor wall, such that the heat-insulating material is trapped between the cylindrical reactor wall and the external induction coil.

4. The reactor vessel according to claim 1 in which the reactor vessel is a ferromagnetic or ferrimagnetic electrically conductive reactor vessel.

5. The reactor vessel according to claim 1 in which the first heating element is an external induction coil which is magnetically coupled to the cylindrical reactor wall of the reactor vessel and which acts as the transmitter, in the process rendering the reactor vessel a receiver.

6. The reactor vessel according to claim 5 in which the external induction coil extends substantially the height of the reactor vessel so as to cover at least most, preferably all, of the cylindrical reactor wall between the reactor base and the removable lid.

7. The reactor vessel according to claim 5 in which the external induction coil is connected to a power supply for inducing eddy currents into the reactor vessel from the external induction coil around the reactor vessel so as to heat a contaminated material load inside the reactor volume by means of radio frequency induction.

8. The reactor vessel according to claim 5 in which the second heating element is an internal induction coil arranged co-axially with the reactor vessel and the external induction coil.

9. The reactor vessel according to claim 8 in which the internal induction coil is located within a blind tube in the center of the reactor vessel.

10. The reactor vessel according to claim 9 in which the blind tube is an elongate metallic tube extending upright through the reactor base and into the reactor volume, positioned coaxially with the reactor vessel and dimensioned to house the internal induction coil therein, the blind tube being closed at its one end which protrudes into the reactor volume, so as to insulate the internal induction coil from a contaminated material load, and being open at its opposite end for receiving the internal induction coil therein.

11. The reactor vessel according to claim 9 in which the reactor vessel also includes one or more conducting plates connected to and extending radially outwardly from the blind tube and the internal induction coil for increasing thermal conduction through a contaminated material load.

12. The reactor vessel according to claim 11 in which the reactor vessel includes four equally spaced conducting plates connected to and extending radially outwardly from the blind tube and terminating in hollow upright tubes located approximate and parallel to the cylindrical reactor wall.

13. The reactor vessel according to claim 8 in which the internal induction coil is connected in series with the external induction coil around the circumference of the reactor vessel, thereby magnetically coupling the external and internal induction coils with the blind tube in the center of the reactor vessel, which creates induced currents into the blind tube, the arrangement being such that heat is transferred radially outwards from the blind tube in the center of the reactor vessel through a contaminated load, as well as radially inwards from the cylindrical reactor wall through the contaminated load.

14. A pyrolysis method for removing and recovering volatilizing contaminants from contaminated materials, while simultaneously minimising residue for final disposal to landfill or incineration, the method being characterised therein that heat is supplied by radio frequency induction of eddy currents, the method comprising the steps of—providing an insulated, electrically conductive reactor vessel according to claim 5;

providing a sealed, batch-driven pyrolysis system;

loading the reactor vessel with a contaminated material load; sealing the reactor vessel with the removable lid;

inducing eddy currents into the reactor vessel, in the absence of oxygen, from the external induction coil for volatilising contaminants within the contaminated material load by means of radio frequency induction heating; and collecting vapour and recoverable products in the condenser as condensates;

the sealed, batch-driven pyrolysis system comprising: an insulated, magnetic, electrically conductive reactor vessel; a vapour extraction system for removing vapours from within the reactor vessel; a condenser arranged in flow communication with the reactor vessel for condensing removed vapours; and a power supply for supplying eddy currents to the reactor vessel so as to heat a contaminated material load inside the reactor volume by means of radio frequency induction; a radio-frequency alternating current being passed between the first heating element and the reactor vessel, in the absence of oxygen, for volatilising the contaminants within the material;

the reactor vessel comprising: a reactor base; a cylindrical reactor wall extending upright from the base; a removable lid dimensioned to rest on the cylindrical reactor wall for sealing the reactor vessel; the reactor base, cylindrical reactor wall and removable lid together defining a reactor volume for holding a contaminated material load; a transmitter in the form of a first heating element arranged approximate a circumference of the reactor vessel and magnetically coupled to the reactor vessel; and at least one exhaust for permitting egress of gasses and steam from the reactor vessel.

15. The method according to claim 14 comprising the additional steps of—providing an inverter with a semiconductor relay which is configured as an H-bridge, the H-bridge including four legs, each of which is associated with a switch, with an output circuit connected across the center of the H-bridge, whereby when two relevant switches are closed, current flows through a contaminated load in one direction, but when the same switches are opened and the opposing two switches closed, current flows in the opposite direction, thus creating current oscillations in the load circuit; and feeding the current oscillations to the external induction coil to create a magnetic coupling between the external induction coil and the reactor vessel (and the internal induction coil inside the vessel, if it is present) through mutual inductance, thereby causing eddy currents to be induced into the reactor vessel from the external induction coil around the reactor vessel, as well as from the internal induction coil in the blind tube in the center of the reactor vessel (if it is present).

16. The method according to claim 14 in which the method is operated under vacuum conditions.

17. A sealed, batch-driven system for removing and recovering volatilizing contaminants from contaminated materials, while simultaneously minimising residue for final disposal to landfill or incineration, the system being characterised therein that it is operated as a pyrolysis system and is heated by radio frequency induction, the system comprising—an insulated, magnetic, electrically conductive reactor vessel according to claim 1;

a vapour extraction system for removing vapours from within the reactor vessel;

a condenser arranged in flow communication with the reactor vessel for condensing removed vapours; and a power supply for supplying eddy currents to the reactor vessel so as to heat a contaminated material load inside the reactor volume by means of radio frequency induction;

the arrangement being such that a radio-frequency alternating current is passed between the first heating element and the reactor vessel, in the absence of oxygen, for volatilising the contaminants within the material.

18. The system according to claim 17 in which the system is operated under conditions that allows for removal and recovery of volatilizing contaminants from contaminated materials for purposes of re-use.

19. The system according to claim 17 in which the power supply includes an AC to DC converter for converting three-phase AC mains supply voltage from a supply frequency of 50 Hz to DC power.

20. The system according to claim 19 in which the converter supplies a variable DC voltage, a fixed DC voltage or a variable DC current.

21. The system according to claim 19 in which the power supply further includes an inverter for converting DC power to single phase AC output.

22. The system according to claim 21 in which DC current is fed to the inverter which converts the DC supply to a single phase AC output at a frequency of between 4 KHz and 100 KHz.

23. The system according to claim 21 in which the inverter includes a semi-conductor relay which is configured as an H-bridge, the H-bridge including four legs, each of which is associated with a switch, with an output circuit connected across the center of the H-bridge, the arrangement being such that when the relevant two switches are closed, current flows through a contaminated load in one direction, but when the same switches are opened and the opposing two switches closed, current flows in the opposite direction, thus creating current oscillations in the load circuit.

24. The system according to claim 17 in which the system includes and is operated under conditions of a vacuum.

* * * * *